(12) United States Patent
Makino et al.

(10) Patent No.: US 10,766,776 B2
(45) Date of Patent: Sep. 8, 2020

(54) SURFACE-MODIFIED NANODIAMOND, ORGANIC SOLVENT DISPERSION THEREOF, AND METHOD FOR PRODUCING SURFACE-MODIFIED NANODIAMOND

(71) Applicant: DAICEL CORPORATION, Osaka-shi, Osaka (JP)

(72) Inventors: Yuto Makino, Himeji (JP); Yoshiyuki Murai, Himeji (JP)

(73) Assignee: DAICEL CORPORATION, Osaka-shi (JP)

( * ) Notice: Subject to any disclaimer, the term of this patent is extended or adjusted under 35 U.S.C. 154(b) by 162 days.

(21) Appl. No.: 16/089,707

(22) PCT Filed: Mar. 24, 2017

(86) PCT No.: PCT/JP2017/012094
§ 371 (c)(1),
(2) Date: Sep. 28, 2018

(87) PCT Pub. No.: WO2017/170251
PCT Pub. Date: Oct. 5, 2017

(65) Prior Publication Data
US 2020/0123012 A1 Apr. 23, 2020

(30) Foreign Application Priority Data

Apr. 1, 2016 (JP) .................. 2016-074518
Apr. 1, 2016 (JP) .................. 2016-074519

(51) Int. Cl.
C07C 231/06 (2006.01)
C01B 32/28 (2017.01)

(52) U.S. Cl.
CPC ............ *C01B 32/28* (2017.08); *C07C 231/06* (2013.01); *C01P 2002/82* (2013.01); *C01P 2004/64* (2013.01)

(58) Field of Classification Search
None
See application file for complete search history.

(56) References Cited

U.S. PATENT DOCUMENTS 6,372,002 B1 * 4/2002 D'Evelyn .............. B24D 3/20
51/293
2005/0008560 A1 1/2005 Kataoka et al.
2008/0318026 A1 12/2008 Dai et al.
2010/0261926 A1 10/2010 Komatsu et al.
2010/0298600 A1 11/2010 Lee

FOREIGN PATENT DOCUMENTS

| CN | 101821196 A | 9/2010 |
|---|---|---|
| JP | 2003-527285 A | 9/2003 |
| JP | 2005-001983 A | 1/2005 |
| JP | 2007-238411 A | 9/2007 |
| JP | 2008-169080 A | 7/2008 |
| JP | 2010-126669 A | 6/2010 |
| JP | 2010-202458 A | 9/2010 |
| JP | 2010-248023 A | 11/2010 |
| JP | 2012-082103 A | 4/2012 |
| KR | 10-2011-0045365 A | 5/2011 |
| WO | WO 01/68521 A2 | 9/2001 |
| WO | WO 2009/060613 A1 | 5/2009 |

OTHER PUBLICATIONS

Barras et al., "Functionalization of Diamond Nanoparticles Using 'Click' Chemistry", Langmuir, vol. 26, No. 16, 2010, pp. 13168-13172.
Extended European Search Report dated Sep. 26, 2019, for Counterpart European Patent Application No. 17774788.8.
Schmidlin et al., "Identification, quantification and modification of detonation nanodiamond functional groups", Diamond and Related Materials, vol. 22, 2012, pp. 113-117.
International Search Report for PCT/JP2017/012094 (PCT/ISA/210) dated May 16, 2017.
Written Opinion of the International Searching Authority for PCT/JP2017/012094 (PCT/ISA/237) dated May 16, 2017.

* cited by examiner

Primary Examiner — Sudhakar Katakam
Assistant Examiner — Jennifer C Sawyer
(74) *Attorney, Agent, or Firm* — Birch, Stewart, Kolasch & Birch, LLP

(57) ABSTRACT

There are provided a surface-modified nanodiamond exhibiting easy dispersibility in an organic solvent, an organic solvent dispersion thereof, and a method for producing the surface-modified nanodiamond. The surface-modified nanodiamond according to the present invention includes a nanodiamond, and a group bound to a particulate surface of the nanodiamond and represented by formula (1):

—NHCOR          (1)

R is an organic group having a carbon atom at a binding site with a neighboring carbonyl carbon atom indicated in the formula; and the left end, in the formula, of the group serves to form bonding to the nanodiamond. The nanodiamond is preferably a detonation nanodiamond or a high-temperature high-pressure nanodiamond.

8 Claims, 3 Drawing Sheets

[FIG. 1]
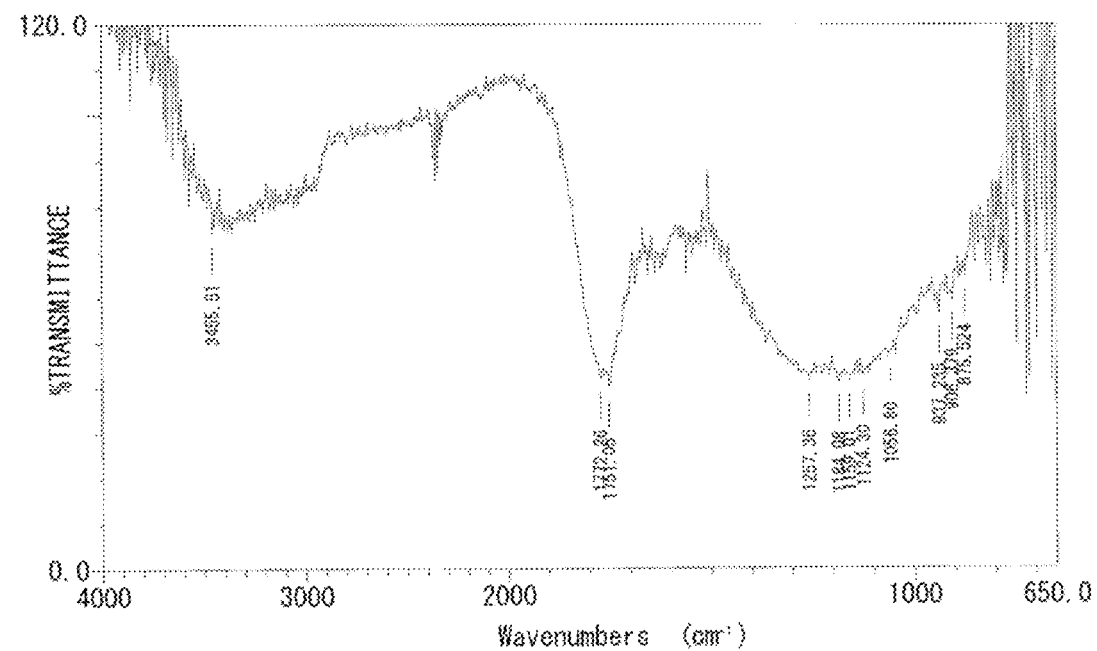
[FIG. 2]
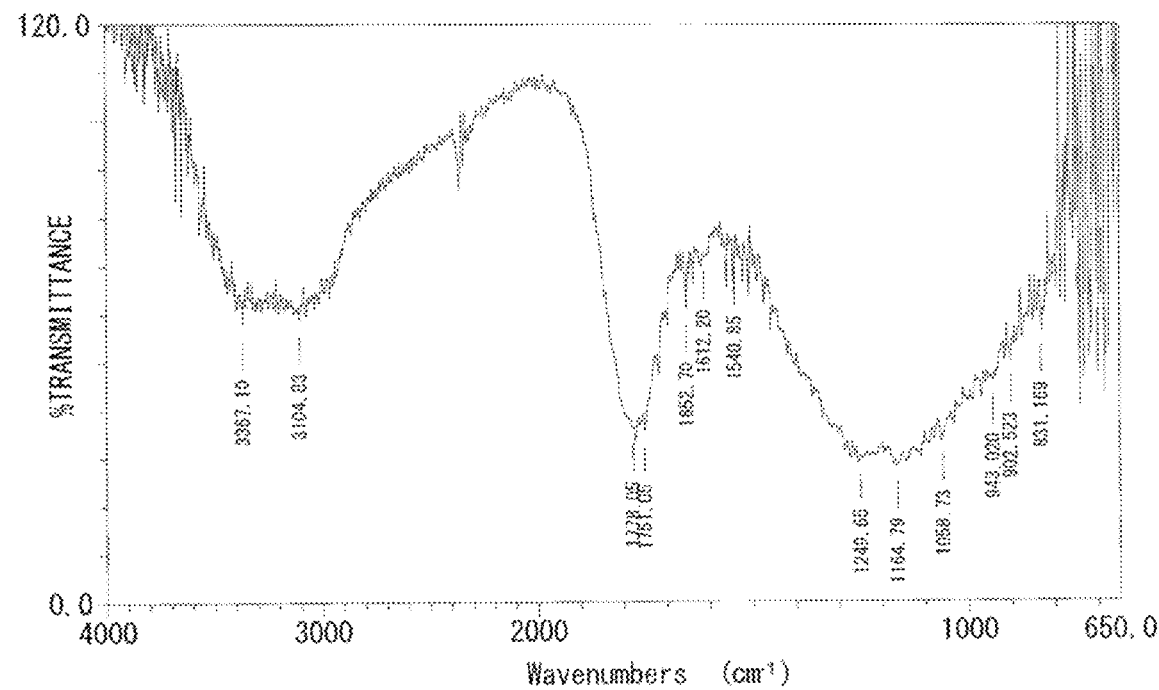

[FIG. 3]
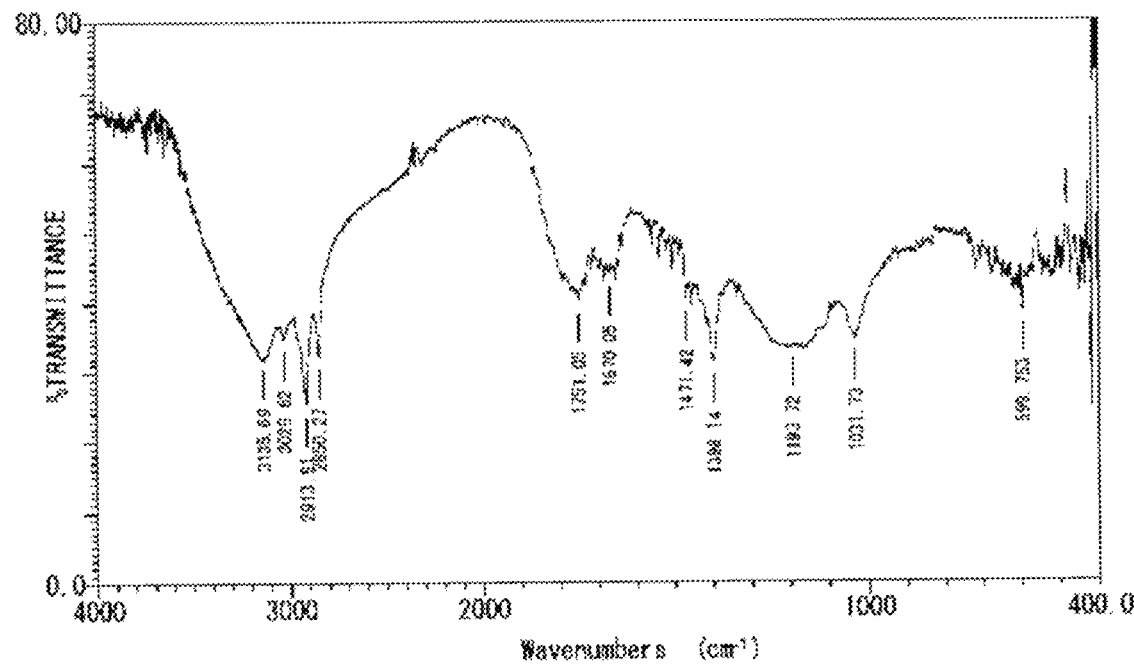
[FIG. 4]
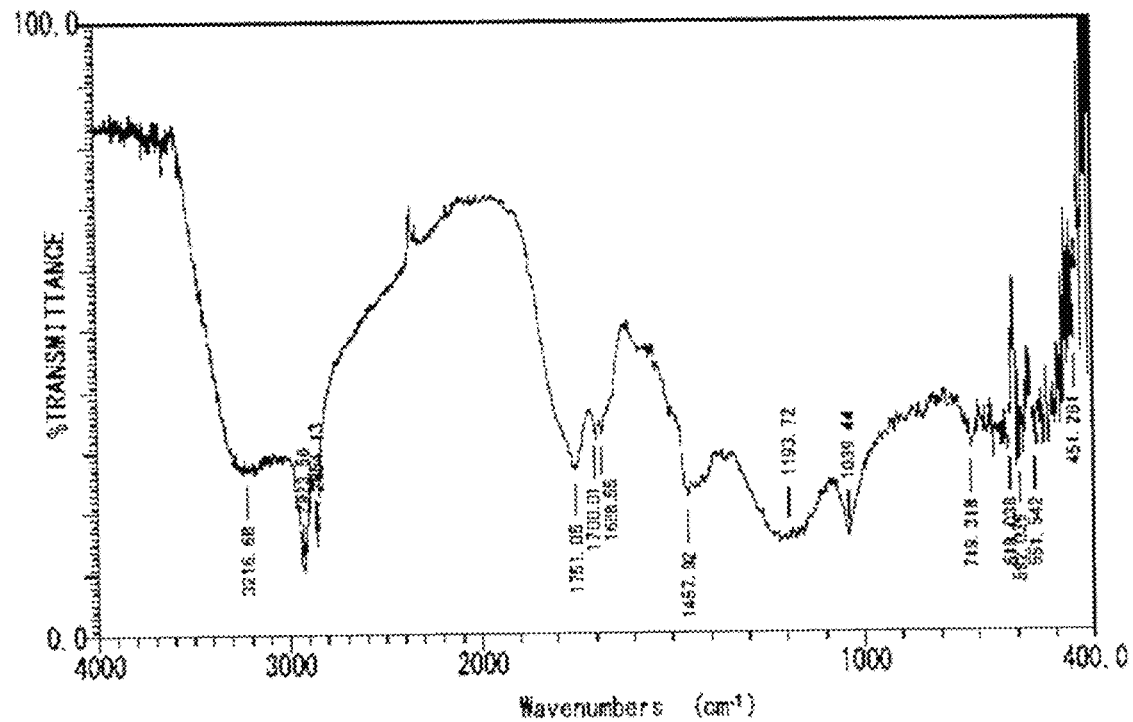

[FIG. 5]
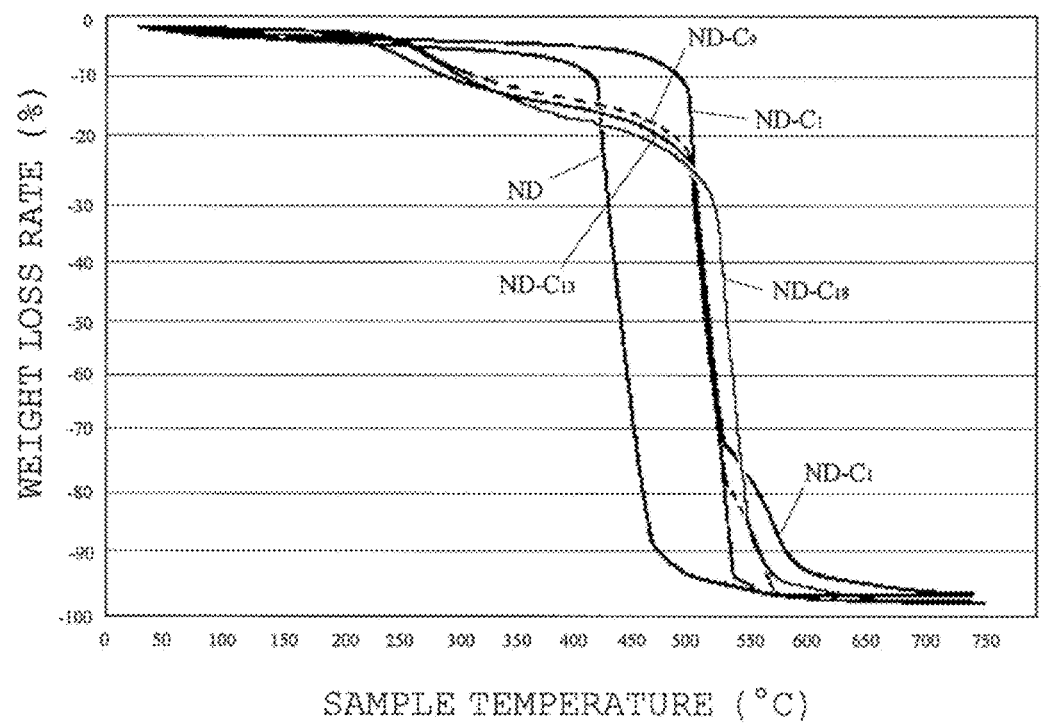

SURFACE-MODIFIED NANODIAMOND, ORGANIC SOLVENT DISPERSION THEREOF, AND METHOD FOR PRODUCING SURFACE-MODIFIED NANODIAMOND

TECHNICAL FIELD

The present invention relates to a surface-modified nanodiamond, an organic solvent dispersion thereof, and a method for producing the surface-modified nanodiamond. The present application claims priority to Japanese Patent Application No. 2016-074518 and Japanese Patent Application No. 2016-074519, filed on Apr. 1, 2016 in Japan, the entire contents of which are hereby incorporated by reference.

BACKGROUND ART

Nanodiamonds are ultrafine diamond particles having a very large specific surface area, and have a high mechanical strength and electric insulation, and an excellent thermoconductivity. The nanodiamonds also have a deodorant effect, an antibacterial effect and a chemical resistance. Hence, the nanodiamonds are used as an abrasive material, an electroconductivity-imparting material, an insulating material, a deodorant, an antibacterial and the like.

Nanodiamonds are usually synthesized by a detonation method. The nanodiamonds obtained by the detonation method forms agglutinates in many cases; the agglutinate is subjected to a deagglutinating treatment using a crusher such as a bead mill to thereby obtain so-called one-digit nanodiamonds having a particle diameter D50 (median diameter) of less than 10 nm (Patent Literatures 1, 2).

CITATION LIST

Patent Literature

Patent Literature 1: Japanese Patent Laid-Open No. 2005-001983
Patent Literature 2: Japanese Patent Laid-Open No. 2010-126669

SUMMARY OF INVENTION

Technical Problem

In water or an aprotic polar organic solvent such as DMSO, DMF or NMP, the nanodiamonds are relatively easily dispersed because the nanodiamonds have polar functional groups on their surfaces, and the polar functional groups and water molecules or molecules of the aprotic polar organic solvent form electric double layers to generate electric repulsion among the nanodiamond. In a protonic polar organic solvent or a nonpolar organic solvent, however, it is very difficult to disperse nanodiamonds because the polar functional groups on the nanodiamond surfaces and molecules of the organic solvent cannot form electric double layers.

As a method of imparting nanodiamonds with the dispersibility thereof in a protonic polar organic solvent or a nonpolar organic solvent, there is conceivably a method of imparting modification groups, having favorable affinity for the protonic polar organic solvent or the nonpolar organic solvent, to the nanodiamond surfaces.

As the method of imparting the surface modification groups, for example, a method of reacting carboxyl groups on the nanodiamond surface with amines or the like to introduce amide groups (—CONHR groups) (for example, National Publication of International Patent Application No. 2003-527285) is known. However, the number of carboxyl groups on the nanodiamond surface is small, and it is difficult for the nanodiamond imparted with the surface modification groups by the method of reaction with the carboxyl groups to exhibit sufficient dispersibility to the organic solvent.

Therefore, an object of the present invention is to provide a surface-modified nanodiamond exhibiting easy dispersibility in an organic solvent. Another object of the present invention is to provide an organic solvent dispersion of the surface-modified nanodiamond. Yet another object of the present invention is to provide a method for producing a surface-modified nanodiamond exhibiting easy dispersibility in an organic solvent.

Solution to Problem

As a result of exhaustive studies to solve the above problem, the present inventors have found that a nanodiamond having —NHCOR groups as surface modification groups, obtained by a reaction of hydroxide groups present in large numbers on the surface of the nanodiamond with nitrile compounds, exhibits easy dispersibility in the organic solvent since the —NHCOR group has excellent affinity for an organic solvent. The present invention has been completed based on this finding.

The present invention provides, in an aspect, a surface-modified nanodiamond. The surface-modified nanodiamond includes a nanodiamond, and a group bound to a particulate surface of the nanodiamond and represented by formula (1):

   (1)

wherein R is an organic group having a carbon atom at a binding site with a neighboring carbonyl carbon atom indicated in the formula; and the left end, in the formula, of the group serves to form bonding to the nanodiamond.

The surface-modified nanodiamond according to the present invention may be a detonation nanodiamond or a high-temperature high-pressure nanodiamond.

In the surface-modified nanodiamond according to the present invention, R in the formula (1) may represent a straight-chain or branched-chain alkyl group having 1 to 22 carbon atoms or a 3- to 22-membered cycloalkyl group.

The present invention provides, in another aspect, an organic solvent dispersion of nanodiamonds. The organic solvent dispersion is made by dispersing the surface-modified nanodiamond (as particles) in an organic solvent.

In the organic solvent dispersion of nanodiamonds, the organic solvent may have an SP value [(cal/cm3)0.5: Fedors calculation value] at 25° C. of 7 to 23.

In the organic solvent dispersion of nanodiamonds, the organic solvent may have a relative permittivity at 25° C. of 1 to 40.

The present invention provides, in yet another aspect, a method for producing a surface-modified nanodiamond. The method includes reacting a nanodiamond with a nitrile compound in the presence of an acid catalyst to obtain the above-mentioned surface-modified nanodiamond, where the nitrile compound is represented by formula (2):

   (2)

wherein R is an organic group having a carbon atom at a binding site with a cyano group indicated in the formula.

In the method for producing the surface-modified nanodiamond, the reaction of the nanodiamond with the nitrile compound represented by the formula (2) may be carried out after a deagglutinating and/or crushing treatment for the nanodiamond or during a deagglutinating and/or crushing treatment for the nanodiamond.

Specifically, the present invention relates to the followings:

A surface-modified nanodiamond including a nanodiamond, and a group bound to a particulate surface of the nanodiamond and represented by formula (1):

—NHCOR (1)

wherein R is an organic group having a carbon atom at a binding site with a neighboring carbonyl carbon atom indicated in the formula; and the left end, in the formula, of the group serves to form bonding to the nanodiamond.

[2] The surface-modified nanodiamond according to [1], wherein the surface-modified nanodiamond is a detonation nanodiamond or a high-temperature high-pressure nanodiamond.

[3] The surface-modified nanodiamond according to [1] or [2], wherein R in the formula (1) represents a hydrocarbon group, a heterocyclic group, or a group in which two or more groups thereof are bound through a single bond or a linkage group.

[4] The surface-modified nanodiamond according to [1] or [2], wherein R in the formula (1) represents a hydrocarbon group.

[5] The surface-modified nanodiamond according to [1] or [2], wherein R in the formula (1) represents a straight-chain or branched-chain alkyl group or a cycloalkyl group, and preferably represents a straight-chain or branched-chain alkyl group having 1 to 22 carbon atoms or a 3- to 22-membered cycloalkyl group.

[6] The surface-modified nanodiamond according to [1] or [2], wherein R in the formula (1) represents a straight-chain or branched-chain alkyl group having 5 to 22 carbon atoms or a cycloalkyl group having 5 to 22 carbon atoms.

[7] The surface-modified nanodiamond according to [1] or [2], wherein R in the formula (1) represents a straight-chain or branched-chain alkyl group, preferably a straight-chain or branched-chain alkyl group having 1 to 22 carbon atoms, and more preferably a straight-chain or branched-chain alkyl group having 5 to 22 carbon atoms.

[8] The surface-modified nanodiamond according to [1] or [2], wherein R in the formula (1) represents a straight-chain alkyl group, preferably a straight-chain alkyl group having 1 to 22 carbon atoms, and more preferably a straight-chain alkyl group having 5 to 22 carbon atoms.

[9] The surface-modified nanodiamond according to any one of [1] to [8], wherein the proportion taken by the weight of the surface modification groups represented by the formula (1) in the total weight of the surface-modified nanodiamond is 0.01 to 30% by weight, preferably 0.5 to 25% by weight, more preferably 5 to 25% by weight, especially preferably 10 to 25% by weight, and most preferably 15 to 25% by weight.

[11] The surface-modified nanodiamond according to any one of [1] to [9], wherein the proportion taken by the weight of the nanodiamonds in the total weight of the surface-modified nanodiamond is 70 to 99.99% by weight, preferably 75 to 99.5% by weight, more preferably 75 to 95% by weight, especially preferably 75 to 90% by weight, and most preferably 75 to 85% by weight.

[11] The surface-modified nanodiamond according to any one of [1] to [10], wherein the surface-modified nanodiamond has a particle diameter D50 of 1000 nm or less, preferably 100 nm or less, and especially preferably 30 nm or less.

[12] An organic solvent dispersion of nanodiamonds, wherein the organic solvent dispersion is made by dispersing the surface-modified nanodiamond according to any one of [1] to [11] in an organic solvent.

[13] The organic solvent dispersion of nanodiamonds according to [12], wherein the organic solvent has an SP value [$(cal/cm^3)^{0.5}$: Fedors calculation value] at 25° C. of 7 to 23, preferably 7 to 17, more preferably 7 to 15, especially preferably 7 to 13, particularly preferably 7 to 12, and most particularly preferably 7 to 10.

[14] The organic solvent dispersion of nanodiamonds according to [12] or [13], wherein the organic solvent has a relative permittivity at 25° C. of 1 to 40, and preferably 2 to 35.

[15] The organic solvent dispersion of nanodiamonds according to any one of [12] to [14], wherein the organic solvent has an SP value [$(cal/cm3)0.5$: Fedors calculation value] at 25° C. of 10.0 or more, preferably 10.0 to 23.0, and especially preferably 10.0 to 15.0; and a relative permittivity at 25° C. of 15 to 40, preferably 15 to 35, and especially preferably 18 to 35.

[16] The organic solvent dispersion of nanodiamonds according to any one of [12] to [15], wherein the organic solvent has an SP value [$(cal/cm^3)^{0.5}$: Fedors calculation value] at 25° C. of less than 10.0, preferably 7.5 to 9.5, and especially preferably 8.0 to 9.3; and a relative permittivity at 25° C. of not less than 1 and less than 15, and preferably 1 to 10, and especially preferably 1 to 5.

[17] The organic solvent dispersion of nanodiamonds according to any one of [12] to [16], wherein the organic solvent is at least one of monohydric alcohols having 1 to 5 carbon atoms and polyhydric alcohols having 2 to 5 carbon atoms.

[18] The organic solvent dispersion of nanodiamonds according to any one of [12] to [16], wherein the organic solvent is at least one selected from the group consisting of methanol, ethanol, 1-propanol, isopropyl alcohol and ethylene glycol.

[19] The organic solvent dispersion of nanodiamonds according to any one of [12] to [16], wherein the organic solvent is at least one selected from the group consisting of toluene, o-xylene, benzene, cyclohexane, n-hexane, carbon tetrachloride, methylene chloride, ethylene dichloride, chloroform, isopropyl ether, tetrahydrofuran, diethyl ether, ethyl acetate, butyl acetate, acetone, methyl ethyl ketone and cyclohexanone.

[20] The organic solvent dispersion of nanodiamonds according to any one of [12] to [19], wherein the nanodiamond concentration in the organic solvent dispersion of nanodiamonds is 0.0001% by weight or more, preferably 0.001% by weight or more, and especially preferably 0.005% by weight or more.

[21] The organic solvent dispersion of nanodiamonds according to any one of [12] to [20], wherein the content of the organic solvent in the total amount of the organic solvent dispersion of nanodiamonds is 85.0 to 99.5% by weight, and preferably 95.0 to 99.5% by weight.

[22] The organic solvent dispersion of nanodiamonds according to any one of [12] to [21], wherein the total content of the surface-modified nanodiamond and the organic solvent in the total amount of the organic solvent dispersion of nanodiamonds is 60% by weight or more, and preferably 90% by weight or more.

[23] The organic solvent dispersion of nanodiamonds according to any one of [12] to [22], including an organic solvent and a surface-modified nanodiamond in a combination, of the following (A) or (B):

(A) a polar organic solvent (particularly a protonic polar organic solvent), and a surface-modified nanodiamond including a nanodiamond and a group, represented by the formula (1), bound to a particulate surface of the nanodiamond, wherein R in the formula (1) is a straight-chain or branched-chain alkyl group having 1 to 9 (preferably 1 to 5) carbon atoms or a cycloalkyl group having 3 to 9 (preferably 3 to 5) carbon atoms; or (B) a nonpolar organic solvent (particularly, an aprotic nonpolar organic solvent), and a surface-modified nanodiamond including a nanodiamond and a group, represented by the formula (1), bound to a particulate surface of the nanodiamond, wherein R in the formula (1) is a straight-chain or branched-chain alkyl group having 9 to 22 (preferably 9 to 18) carbon atoms or a cycloalkyl group having 9 to 22 (preferably 9 to 18) carbon atoms.

[24] The organic solvent dispersion of nanodiamonds according to any one of [12] to [23], wherein the particle diameter D50 of the nanodiamonds in the organic solvent dispersion of nanodiamonds is 1000 nm or less, preferably 800 nm or less, and especially preferably 700 nm or less.

[25] A method for producing a surface-modified nanodiamond, including reacting a nanodiamond with a nitrile compound in the presence of an acid catalyst to obtain the surface-modified nanodiamond according to any one of [1] to [11], the nitrile compound being represented by formula (2):

R-CN    (2)

wherein R is an organic group having a carbon atom at a binding site with a cyano group indicated in the formula.

[26] The method for producing a surface-modified nanodiamond according to [25], wherein the reaction of the nanodiamond with the nitrile compound represented by the formula (2) is carried out after a deagglutinating and/or crushing treatment for the nanodiamond or during a deagglutinating and/or crushing treatment for the nanodiamond.

ADVANTAGEOUS EFFECTS OF INVENTION

The surface-modified nanodiamond according to the present invention exhibits easy dispersibility in the organic solvent since the -NHCOR group or groups on the nanodiamond surface has excellent affinity for an organic solvent. Hence, subjecting a mixture of the surface-modified nanodiamond according to the present invention and the organic solvent to a dispersion treatment can give an organic solvent dispersion of nanodiamonds which contains nanodiamonds in a highly dispersed state.

Further, the method for producing a surface-modified nanodiamond according to the present invention can produce the above surface-modified nanodiamond efficiently.

Then, the organic solvent dispersion of nanodiamonds is excellent in compatibility with oil agents and resin compositions, and, even when being added to the oil agents or resin compositions, can serve to maintain high dispersibility of the nanodiamonds. Further, the organic solvent dispersion of nanodiamonds contains nanodiamonds collectively having a high mechanical strength and electric insulation, and an excellent thermoconductivity, deodorant effect, antibacterial effect, and chemical resistance. Hence, compositions obtained by adding the organic solvent dispersion to oil agents or resin compositions can highly develop the characteristics originated from the nanodiamonds, and are suitably used as, for example, heat radiating materials, optical materials (for example, high-functional film materials), material-reinforcing materials, heat exchange fluid media, coating materials (for example, antibacterial coating materials and deodorant coating materials), abrasive materials, lubricants, and medical materials.

BRIEF DESCRIPTION OF DRAWINGS

FIG. 1 is a diagram showing a vacuum/heated IR measurement result of the nanodiamond powder (ND) obtained in Preparation Example 1.

FIG. 2 is a diagram showing a vacuum/heated IR measurement result of the surface-modified nanodiamond (ND-$C_1$) obtained in Example 1.

FIG. 3 is a diagram showing a vacuum/heated IR measurement result of the surface-modified nanodiamond (ND-$C_9$) obtained in Example 2.

FIG. 4 is a diagram showing a vacuum/heated IR measurement result of the surface-modified nanodiamond (ND-$C_{18}$) obtained in Example 4.

FIG. 5 is a diagram showing thermogravimetry results of the nanodiamond powder (ND) obtained in Preparation Example 1 and the surface-modified nanodiamonds (ND-$C_1$), (ND-$C_9$), (ND-$C_{13}$) and (ND-$C_{18}$) obtained in Examples.

DESCRIPTION OF EMBODIMENTS

Surface-modified nanodiamond

The surface-modified nanodiamond according to one embodiment of the present invention includes nanodiamonds and groups each represented by formula (1):

—NHCOR  (1)

wherein R is an organic group having a carbon atom at a binding site with a neighboring carbonyl carbon atom indicated in the formula; and the left end, in the formula, of the group serves to form bonding to the nanodiamond. The group (hereinafter, referred to as "surface modification group" in some cases) is bound to the particulate surface of the nanodiamond. The nanodiamonds are each accompanied by the group or groups.

The organic group as the R includes hydrocarbon groups, heterocyclic groups, and groups in which two or more groups thereof bound through a single bond or a linkage group (divalent group having one or more atoms). Examples of the linkage group include a carbonyl group (—CO—), an ether bond (—O—), a thioether bond (—S—), an ester bond (—COO—), an amide bond (—CONH—), a carbonate bond (—OCOO—), and groups in which a plurality thereof are linked.

The hydrocarbon group includes aliphatic hydrocarbon groups, alicyclic hydrocarbon groups, aromatic hydrocarbon groups, and groups in which these are bound.

The aliphatic hydrocarbon group is preferably an aliphatic hydrocarbon group having 1 to 22 carbon atoms, and examples thereof include straight-chain or branched-chain alkyl groups having 1 to 22 (the upper limit is preferably 20, more preferably 19, and especially preferably 18; and the lower limit is preferably 3, especially preferably 5, and most preferably 8) carbon atoms, such as a methyl group, an ethyl group, a propyl group, an isopropyl group, a butyl group, an isobutyl group, an s-butyl group, a t-butyl group, a pentyl group, a hexyl group, a decyl group, and a dodecyl group; alkenyl groups having 2 to 22 (preferably 2 to 10, and especially preferably 2 or 3) carbon atoms, such as a vinyl group, an allyl group, and 1-butenyl group; and alkynyl groups having 2 to 22 (preferably 2 to 10, and especially preferably 2 or 3) carbon atoms, such as an ethynyl group, and a propynyl group.

The alicyclic hydrocarbon group is preferably a 3-to 22-membered alicyclic hydrocarbon group, and examples thereof include about 3- to 22-membered (preferably 3- to 18-membered, more preferably 3- to 15-membered, and especially preferably 5- to 8-membered) cycloalkyl groups, such as a cyclopropyl group, a cyclobutyl group, a cyclopentyl group, a cyclohexyl group, and a cyclooctyl group; about 3- to 22-membered (preferably 3- to 15-membered, and especially preferably 5- to 8-membered) cycloakenyl groups, such as a cyclopentenyl group, and a cyclohexenyl group; and crosslinked cyclic hydrocarbon groups, such as a perhydronaphthalen-1-yl group, a norbornyl group, an adamantyl group, a tricyclo[5.2.1.0$^{2,6}$] decan-8-yl group, and a tetracyclo[4.4.0.1$^{2,5}$.1$^{7,10}$]dodecan-3-yl group.

The aromatic hydrocarbon group is preferably an aromatic hydrocarbon group having 6 to 14 (particularly 6 to 10) carbon atoms, and examples thereof include a phenyl group, and a naphthyl group.

The above hydrocarbon groups may have various types of substituents [for example, a halogen atom, an oxo group, a hydroxyl group, a substituted oxy group (for example, an alkoxy group, an aryloxy group, an aralkyloxy group, and an acyloxy group), a carboxyl group, a substituted oxycarbonyl group (for example, an alkoxycarbonyl group, an aryloxycarbonyl group, and an aralkyloxycarbonyl group), a substituted or unsubstituted carbamoyl group, a cyano group, a nitro group, a substituted or unsubstituted amino group, a sulfo group, a heterocyclic group, and the like]. The hydroxyl group and the carboxyl group may be protected with a blocking group commonly used in the organic synthesis field. Rings of the alicyclic hydrocarbon groups and the aromatic hydrocarbon groups may be condensed with an aromatic or non-aromatic heterocycle.

In the case where the hydrocarbon group is a cycloalkyl group, the cycloalkyl group may further have, as substituents, one or more straight-chain or branched-chain alkyl groups having about 1 to 15 carbon atoms.

The heterocyclic group is a group obtained by eliminating one hydrogen atom from the structural formula of a heterocycle, and the heterocycle includes aromatic heterocycles and non-aromatic heterocycles. Examples of such heterocycles include 3- to 10-membered (preferably 4- to 6-membered) rings having, as atoms constituting the ring, carbon atoms and at least one heteroatom (for example, an oxygen atom, a sulfur atom, or a nitrogen atom), and condensed rings thereof. Specifically, examples of the heterocycle include heterocycles containing an oxygen atom as a heteroatom (for example, 3-membered rings such as an oxirane ring; 4-membered rings such as an oxetane ring; 5-membered rings such as a furan ring, a tetrahydrofuran ring, an oxazole ring, an isoxazole ring, and a γ-butyrolactone ring; 6-membered rings such as a 4-oxo-4H-pyran ring, a tetrahydropyran ring, and a morpholine ring; condensed rings such as a benzofuran ring, an isobenzofuran ring, a 4-oxo-4H-chromene ring, a chroman ring, and an isochroman ring; and crosslinked rings such as a 3-oxatricyclo[4.3.1.1$^{4,8}$] undecan-2-one ring, and a 3-oxatricyclo[4.2.1.0$^{4,8}$] nonan-2-one ring), heterocycles containing a sulfur atom as a heteroatom (for example, 5-membered rings such as a thiophene ring, a triazole ring, an isothiazole ring, and a thiadiazole ring; 6-membered rings such as 4-oxo-4H-thiopyran rings; and condensed rings such as a benzothiophene ring), and heterocycles containing a nitrogen atom as a heteroatom (for example, 5-membered rings such as a pyrrole ring, a pyrrolidine ring, a pyrazole ring, an imidazole ring, and a triazole ring; 6-membered rings such as an isocyanuric ring, a pyridine ring, a pyridazine ring, a pyrimidine ring, a pyrazine ring, a piperidine ring, and a piperazine ring; and condensed rings such as an indole ring, an indoline ring, a quinoline ring, an acridine ring, a naphthyridine ring, a quinazoline ring, and a purine ring). The heterocyclic group may have, in addition to the substituents that the above-mentioned hydrocarbon group may have, $C_{1-4}$ alkyl groups (for example, a methyl group and an ethyl group), $C_{3-20}$ cycloalkyl groups, and $C_{6-14}$ aryl groups (for example, a phenyl group and a naphthyl group).

Among these, the R is, in the point of being capable of exhibiting excellent dispersibility in an organic solvent, preferably a hydrocarbon group, more preferably a straight-chain or branched-chain alkyl group or a cycloalkyl group, especially preferably a straight-chain or branched-chain alkyl group having 1 to 22 carbon atoms or a cycloalkyl group having 3 to 22 carbon atoms, and most preferably a straight-chain or branched-chain alkyl group or cycloalkyl group having 5 to 22 carbon atoms.

The R is especially preferably a straight-chain or branched-chain alkyl group, most preferably a straight-chain or branched-chain alkyl group having 1 to 22 carbon atoms, and particularly preferably a straight-chain or branched-chain alkyl group having 5 to 22 carbon atoms.

The nanodiamond to which the group represented by the above formula (1) is bound is preferably a detonation nanodiamond (that is, a nanodiamond produced by a detonation method) and a high-temperature high-pressure nanodiamond (that is, a nanodiamond produced by a high-temperature high-pressure method), and of these, the nanodiamond is preferably the detonation nanodiamond in that the particle diameter of the nanodiamond primary particles is in the one-digit nanometer range. The detonation nanodiamond known in the art includes an air-cooled type detonation nanodiamond and a water-cooled type detonation nanodiamond, of these, an air-cooled type detonation nanodiamond is preferable. The air-cooled type detonation nanodiamond is likely to have a smaller primary particle than the water-cooled type detonation nanodiamond.

The particle diameter D50 (median diameter: 50-vol % diameter) of the surface-modified nanodiamond (as particles) according to the present invention is, for example, 1000 nm or less, preferably 100 nm or less, and especially preferably 30 nm or less. The lower limit of the particle diameter D50 of the surface-modified nanodiamond is, for example, 4 nm. Here, in the present description, the "particle diameter D50" is measured by a so-called dynamic light scattering method.

The proportion of the weight of the surface modification groups taken in the total amount of the surface-modified nanodiamond according to the present invention is, for example, 0.01 to 30% by weight, preferably 0.5 to 25% by weight, more preferably 5 to 25% by weight, especially preferably 10 to 25% by weight, and most preferably 15 to 25% by weight. Further, the proportion of the weight of the nanodiamonds taken in the total amount of the surface-modified nanodiamond according to the present invention is, for example, 70 to 99.99% by weight, preferably 75 to 99.5% by weight, more preferably 75 to 95% by weight, especially preferably 75 to 90% by weight, and most preferably 75 to 85% by weight. Here, each weight of the surface modification group moiety and the nanodiamond moiety in the surface-modified nanodiamond can be determined, for example, by subjecting the surface-modified nanodiamond to a thermogravimetry and using weight loss rates in a specific temperature range. In detail, when the surface-modified nanodiamond is subjected to a thermogravimetry in an air atmosphere, weight losses are observed in the temperature range of not less than 200° C. and less than 500° C. This is caused by thermal decomposition of the surface modification group moiety in the surface-modified nanodiamond. Therefore, the weight loss rate in the above temperature range corresponds to a proportion taken by the surface modification group moiety in the total amount of the surface-modified nanodiamond. Then, the weight sharply reduces at 500° C. or more (for example, 500 to 600° C.) This is caused by thermal decomposition of the nanodiamond moiety in the surface-modified nanodiamond. Therefore, the weight loss rate in the above temperature range corresponds to a proportion taken by the nanodiamond moiety in the total amount of the surface-modified nanodiamond.

The surface-modified nanodiamond according to the present invention, which has the above-described configuration, can exhibit easy dispersibility in an organic solvent (even in a protonic polar organic solvent or a nonpolar organic solvent, in which dispersion is conventionally very difficult). With the surface-modified nanodiamond according to the present invention, the organic solvent dispersion of nanodiamonds which contains primary particles of nanodiamond in a highly dispersed state in an organic solvent.

Method for producing the surface-modified nanodiamond

The surface-modified nanodiamond can be produced, for example, by reacting a nanodiamond with a nitrile compound represented by formula (2):

R—CN (2)

in the presence of an acid catalyst.

The R in the above formula (2) is an organic group having a carbon atom at a binding site with a cyano group indicated in the formula, and corresponds to the R in the above formula (1).

As a nanodiamond to be subjected to a surface modification step, for example, a detonation nanodiamond (that is, a nanodiamond produced by a detonation method) or a high-temperature high-pressure nanodiamond (that is, a nanodiamond produced by a high-temperature high-pressure method) may be used. In the present invention, of these, use of the detonation nanodiamond is preferable for being better in dispersibility, or in that the particle diameter of the primary particle is in the one-digit nanometer range.

The detonation method includes an air-cooled type detonation method and a water-cooled type detonation method. In the present invention, of these, the air-cooled type detonation method is preferable to the water-cooled type detonation method because the former is capable of providing a nanodiamond having smaller primary particles. Therefore, a nanodiamond to be subjected to the surface modification step is preferably a detonation nanodiamond, that is, a nanodiamond produced by a detonation method, and more preferably an air-cooled type detonation nanodiamond, that is, a nanodiamond produced by an air-cooled type detonation method.

The detonation nanodiamond can be produced, for example, through the steps of (1) a formation step, (2) a refinement step (including an acid treatment, an oxidation treatment and a pre-treatment for deagglutinating), (3) a pH adjustment step, (4) a deagglutinating treatment step, (5) a centrifugal separation step, and (6) a drying step.

(1) Formation Step

In the air-cooled type detonation method, first, a molded explosive installed with an electric detonator is placed in the interior of a pressure vessel for detonation. The vessel to be used is, for example, a metal-made vessel such as an iron-made vessel. The volume of the vessel is, for example, 0.5 to 40 m³, and preferably 2 to 30 m³. The explosive usable is a mixture of trinitrotoluene (TNT) with cyclotrimethylenetrinitroamine, that is, hexogen (RDX). The weight ratio (TNT/RDX) of TNT and RDX is, for example, in the range of 40/60 to 60/40.

In the formation step, then, the electric detonator is initiated to detonate the explosive in the vessel. The detonation refers to, among explosions accompanying chemical reactions, an explosion in which the flame front causing reactions moves at a high speed exceeding the sound velocity. In the detonation, the explosive in use partially causes incomplete combustion and isolates carbon; and with the isolated carbon as a raw material, a crude nanodiamond is produced by the action of the pressure of shock waves and the energy generated by the explosion.

The detonation may be carried out in the air atmosphere, or may be carried out in an inert gas atmosphere such as a nitrogen atmosphere or an argon atmosphere.

In the formation step, then, the vessel is left to stand at room temperature for 24 hours to thereby cause the temperature of the vessel and its interior to be lowered. After this natural cooling, the crude nanodiamond (containing nanodiamonds and impurities) adhered on the inner wall of the vessel is scraped off with a spatula to thereby recover the crude nanodiamond. The recovered crude nanodiamond aggregates very firmly due to a contribution of the action of the van der Waals force among neighboring primary particles and crystallites and additionally a contribution of the coulomb interaction among crystal planes, and froms agglutinates.

The recovered crude nanodiamond contains oxides of metals such as Al, Fe, Co, Cr and Ni contained in the vessel and the like used for the formation reaction (for example, $Fe_2O_3$, $Fe_3O_4$, $Co_2O_3$, $Co_3O_4$, NiO, $Ni_2O_3$ and the like) as metallic impurities, and the metallic impurities cause agglutination of nanodiamonds. There is further a case where the recovered crude nanodiamond contains by-products such as graphite, and this also causes agglutination of nanodiamonds.

(2) Refinement Step (Acid Treatment Step)

The acid treatment step is a step of removing the metallic impurities contaminating the crude nanodiamond obtained through the formation step, and can remove the metallic impurities by adding an acid to a crude nanodiamond water dispersion obtained by dispersing the crude nanodiamond obtained through the formation step in water to thereby cause the metallic impurities to dissolve in the acid, and thereafter separating and removing the acid containing the metallic impurities dissolving therein. The acid (particularly a strong acid) to be used for the acid treatment is preferably a mineral acid, examples of which include hydrochloric acid, hydrofluoric acid, sulfuric acid, nitric acid, and an aqua regia. These can be used singly or in a combination of two or more. The concentration of the acid to be used in the acid treatment is, for example, 1 to 50% by weight. The acid treatment temperature is, for example, 70 to 150° C. The acid treatment time is, for example, 0.1 to 24 hours. Further, the acid treatment is allowed to be carried out under reduced pressure, under normal pressure or under pressure. It is preferable that a method of separating and removing the acid containing the metallic impurities dissolving therein involves separating and removing, for example, by decantation. Then, it is preferable that in the decantation, water washing of solid contents (including nanodiamonds) is carried out, and it is especially preferable to carry out water washing repeatedly until the pH of a precipitate liquid becomes, for example, 2 to 3.

(2) Refinement Step (Oxidation Treatment Step)

The oxidation treatment step is a step of removing graphite contaminating the crude nanodiamond obtained through the formation step. The graphite is originated from carbon which has not formed nanodiamond crystals, out of carbons liberated from the explosive as a result of partial incomplete combustion. The graphite can be removed, for example, by causing an oxidizing agent to act on a crude nanodiamond water dispersion obtained by dispersing, in water, the crude nanodiamond obtained through the formation step (preferably the nanodiamond water dispersion obtained through the above acid treatment step). Examples of the oxidizing agent include chromic acid, chromic acid anhydride, dichromic acid, permanganic acid, perchloric acid, and salts thereof. These can be used singly or in a combination of two or more. The concentration of the oxidizing agent to be used for the oxidation treatment is, for example, 3 to 50% by weight. The used amount of the oxidizing agent in the oxidation treatment is, for example, 300 to 500 parts by weight with respect to 100 parts by weight of the crude nanodiamond to be subjected to the oxidation treatment. The oxidation treatment temperature is, for example, 100 to 200° C. The oxidation treatment time is, for example, 1 to 24 hours. The oxidation treatment may be carried out under reduced pressure, under normal pressure or under pressure. Then, it is preferable, from the viewpoint of improving the removal efficiency of the graphite, that the oxidation treatment is carried out in the coexistence of an acid (particularly a mineral acid, including the same mineral acids as in use in the acid treatment). In the case where an acid is used for the oxidation treatment, the concentration of the acid is, for example, 5 to 80% by weight. After such an oxidation treatment, it is preferable that water washing of solid contents (containing nanodiamond agglutinate) is carried out, for example, by decantation. An initial supernatant liquid of the water washing is colored, but it is preferable that water washing of the solid contents by decantation is repeatedly carried out until the supernatant liquid visually becomes transparent.

(2) Refinement Step (Pre-Treatment Step For Deagglutinating)

The pre-treatment step for deagglutinating is a step of reacting a solution containing the nanodiamond agglutinates obtained through the oxidation treatment step with an alkali and hydrogen peroxide. Examples of the alkali include sodium hydroxide, ammonia, and potassium hydroxide. The concentration of the alkali is preferably 0.1 to 10% by weight, more preferably 0.2 to 8% by weight, and still more preferably 0.5 to 5% by weight. The concentration of the hydrogen peroxide is preferably 1 to 15% by weight, more preferably 2 to 10% by weight, and still more preferably 4 to 8% by weight. The temperature when the reaction is carried out is, for example, 40 to 95° C.; and the reaction time is, for example, 0.5 to 5 hours. Further, the reaction may be carried out under reduced pressure, under normal pressure or under pressure. After the reaction, it is preferable that a supernatant is removed by decantation.

(3) pH adjustment step

The pH adjustment step is a step of adjusting the nanodiamond water dispersion having been subjected to the above-mentioned refinement steps to a predetermined pH. In the present step, it is preferable that the pH is adjusted by adding an acid or an alkali (for example, sodium hydroxide) to a precipitate liquid after the decantation. It is preferable, from the viewpoint of disperse stability of the nanodiamonds, that the pH is adjusted, for example, to 8 or more (for example, 8 to 12), preferably 9 or more (for example, 9 to 11), and more preferably 9.5 to 10.5.

(4) Deagglutinating Treatment Step

The deagglutinating treatment step is a step of subjecting the nanodiamond water dispersion having been subjected to the above steps to a deagglutinating and/or crushing treatment to thereby deagglutinate (disintegrate) or crush the nanodiamond agglutinate contained in the nanodiamond water dispersion to nanodiamond primary particles. The deagglutinating and/or crushing treatment can be carried out, for example, by using a high shear mixer, a homomixer, a ball mill, a bead mill, a high-pressure homogenizer, an ultrasonic homogenizer, or a colloid mill.

(5) Centrifugal Separation Step

The centrifugal separation step is a step of subjecting the nanodiamond water dispersion obtained through the above-mentioned steps to a centrifugal separation treatment to thereby obtain a predetermined supernatant liquid. Specifically, after a precipitate and the supernatant liquid formed by the centrifugal separation treatment using a centrifugal separator are divided, the precipitate is mixed with water and suspended, and further subjected to a centrifugal separation treatment using a centrifugal separator to carry out solid-liquid separation. The amount of the water to be added is, for example, 3 to 5 times (volume ratio) that of the precipitate. It is preferable that a series of processes of separation of a precipitate and a supernatant liquid after solid-liquid separation by centrifugal separation, addition of ultrapure water to the precipitate and suspending, and further centrifugal separation treatment is repeatedly carried out until after the centrifugal separation treatment, a black transparent supernatant liquid is obtained. Then, the centrifugal force in the centrifugal separation treatment is, for example, 15000 to 25000×g; and the centrifugal time is, for example, 10 to 120 mins.

(6) Drying Step

The drying step is a step of subjecting the nanodiamond water dispersion having been subjected to the above-mentioned steps to a drying treatment to thereby obtain dried powder of the nanodiamond. Examples of means of the drying treatment include spray drying carried out by using a spray drying apparatus and evaporating to dryness carried out by using an evaporator.

(7) Surface Modification Step

The surface modification step is a step of reacting the nanodiamond with a nitrile compound represented by the above formula (2) in the presence of an acid catalyst, specifically, reacting hydroxide groups present on the nanodiamond surface with the nitrile compound as in the Ritter reaction.

The nanodiamond generally has hydroxide groups on its surface. Then, when the nanodiamond and a nitrile compound represented by the formula (2) are reacted in the presence of an acid catalyst, the nitrile compound represented by the formula (2) reacts with hydroxide groups present on the surface of the nanodiamond and forms surface modification groups represented by the above formula (1).

Then, it is preferable that a nitrile compound represented by the formula (2) is selected and used according to the kind of an organic solvent in which the nanodiamond particles are desired to exhibit easy dispersibility. For example, in the case where the organic solvent in which the nanodiamond particles are desired to exhibit easy dispersibility is a polar organic solvent (particularly a protonic polar organic solvent) described later, it is preferable to use a nitrile compound in which R in the formula (2) is a straight-chain or branched-chain alkyl group having 1 to 9 (preferably 1 to 5) carbon atoms or a cycloalkyl group having 3 to 9 (preferably 3 to 5) carbon atoms. Further, in the case where the organic solvent in which the nanodiamond particles are desired to exhibit easy dispersibility is a nonpolar organic solvent (particularly an aprotic nonpolar organic solvent) described later, it is preferable to use a nitrile compound in which R in the formula (2) is a straight-chain or branched-chain alkyl group having 9 to 22 (preferably 9 to 18) carbon atoms or a cycloalkyl group having 9 to 22 (preferably 9 to 18) carbon atoms.

The nanodiamond to be subjected to the surface modification step may be nanodiamond powder or may also be a water dispersion of the nanodiamond, but the nanodiamond powder is preferable in that the reactivity with the nitrile compound is excellent, and a surface-modified nanodiamond can be produced efficiently.

Then, the particle diameter D50 (median diameter) of the nanodiamonds to be subjected to the surface modification step is, for example, 5000 nm or less, preferably 100 nm or less, especially preferably 10 nm or less, and most preferably less than 10 nm. The lower limit of the particle diameter D50 of the nanodiamonds is, for example, 1 nm.

The used amount of the nitrile compound represented by the formula (2) is, with respect to 100 parts by weight of the nanodiamonds, for example, about 200 to 10000 parts by weight, preferably 300 to 5000 parts by weight, and especially preferably 500 to 2000 parts by weight. When the nitrile compound represented by the formula (2) is used in the above range, easy dispersibility in an organic solvent can be imparted to the nanodiamonds. When the used amount of the nitrile compound represented by the formula (2) is below the aforementioned range, it is likely to become difficult to sufficiently impart the dispersibility in an organic solvent to the nanodiamonds. On the other hand, when the used amount of the nitrile compound represented by the formula (2) exceeds the aforementioned range, separation and removal of by-products is likely to become difficult.

The above reaction is carried out in the presence of an acid catalyst. As the acid catalyst, one or two or more selected from, for example, a concentrated sulfuric acid (sulfuric acid concentration: 95 to 98% by weight) and a boron trifluoride diethyl ether complex may be suitably used. The used amount (in the case of using two or more kinds, the total amount) of the acid catalyst is, with respect to 100 parts by weight of the nanodiamonds, for example, about 50 to 1000 parts by weight, preferably 70 to 500 parts by weight, especially preferably 90 to 350 parts by weight, particularly preferably 100 to 350 parts by weight, and most particularly preferably 150 to 350 parts by weight.

The reaction atmosphere is not especially limited as long as the reaction atmosphere does not inhibit the reaction, and may be any of, for example, an air atmosphere, a nitrogen atmosphere, and an argon atmosphere.

The reaction temperature is, for example, about room temperature to 200° C. The reaction time is, for example, about 1 to 10 hours. Further, the reaction can be carried out in any method of a batch system, a semi-batch system, a continuous system, and the like.

The above reaction is preferably carried out after the deagglutinating and/or crushing treatment of the nanodiamonds by means such as ultrasonic treatment or bead milling, or while the deagglutinating and/or crushing treatment of the nanodiamonds by the means described above, from the viewpoint of causing hydroxide groups present on the primary particle surface of the nanodiamond and the nitrile compound represented by the formula (2) to react, and of obtaining a surface-modified nanodiamond capable of exhibiting higher dispersibility in an organic solvent. It is particularly preferable to carry out the reaction after the deagglutinating and/or crushing treatment of the nanodiamonds by the means described above.

It is preferable that after the finish of the reaction, an obtained reaction product is subjected to a refinement treatment by, for example, filtration, centrifugal separation, extraction, water washing, neutralization, or combined means thereof.

Then, by subjecting the reaction product after the refinement treatment to the drying treatment, powder of a surface-modified nanodiamond is obtained. Examples of means of the drying treatment include reduced-pressure heat drying (including spray drying carried out by using a spray drying apparatus under reduced pressure and evaporation to dryness carried out by using an evaporator under reduced pressure).

Organic Solvent Dispersion of Nanodiamonds

The organic solvent dispersion of nanodiamonds according to the present invention is so configured that the above surface-modified nanodiamond is dispersed in an organic solvent. The organic solvent dispersion of nanodiamonds according to the present invention can be produced, for example, by mixing the surface-modified nanodiamond with an organic solvent, subjecting the mixture to a dispersion treatment by ultrasonic treatment, bead milling or the like, and subjecting the resultant to a refinement treatment including filtration treatment, centrifugal separation treatment and the like, as required.

The organic solvent includes protonic organic solvents and aprotic organic solvents, and includes polar organic solvents and nonpolar organic solvents. These can be used singly or in a combination of two or more.

The SP value [$(cal/cm^3)^{0.5}$: Fedors calculation value] at 25° C. of the organic solvent is, for example, 7 to 23 (preferably 7 to 17, more preferably 7 to 15, especially preferably 7 to 13, particularly preferably 7 to 12, and most particularly preferably 7 to 10).

Further, the relative permittivity at 25° C. of the organic solvent is, for example, 1 to 40 (preferably 2 to 35). Here, the relative permittivities in the present description are values described in Chemical Handbook, 5th ed., Basic, Maruzen Bookstores Co., The Chemical Society of Japan, ed. (in Japanese). The relative permittivity can also be determined by injecting an organic solvent in a glass cell with ITO transparent electrodes of 10 μm in cell gap, and measuring an electric capacity of the prepared cell at 25° C. and 40% RH by using an LCR meter (measurement frequency: 1 kHz), model number: 2353, manufactured by NF Corp.

The SP value at 25° C. of the polar organic solvent is, for example, 10.0 or more (preferably 10.0 to 23.0, and especially preferably 10.0 to 15.0); and the SP value at 25° C. of the nonpolar organic solvent is, for example, less than 10.0 (preferably 7.5 to 9.5, and especially preferably 8.0 to 9.3). Further, the relative permittivity at 25° C. of the polar organic solvent is, for example, 15 to 40 (preferably 15 to 35, and especially preferably 18 to 35); and the relative permittivity at 25° C. of the nonpolar organic solvent is, for example, 1 or more and less than 15 (preferably 1 to 10, and especially preferably 1 to 5).

Examples of the protonic organic solvent include monohydric alcohols having 1 to 5 carbon atoms such as methanol (SP value: 13.8, relative permittivity: 32.6), ethanol (SP value: 12.6, relative permittivity: 24.30), 1-propanol (SP value: 11.8, relative permittivity: 20.1), and isopropyl alcohol (SP value: 11.6, relative permittivity: 19.92); and polyhydric alcohols having 2 to 5 carbon atoms such as ethylene glycol.

Examples of the aprotic organic solvent include aromatic hydrocarbons such as toluene (SP value: 9.14, relative permittivity: 2.379), o-xylene (SP value: 9.10), and benzene; alicyclic hydrocarbons such as cyclohexane; aliphatic hydrocarbons such as n-hexane (SP value: 7.29); halogenated hydrocarbons such as carbon tetrachloride, methylene chloride, ethylene dichloride, and chloroform; ethers such as isopropyl ether, tetrahydrofuran (SP value: 8.28), and diethyl ether (SP value: 7.25); esters such as ethyl acetate (SP value: 8.75), and butyl acetate (SP value: 8.70); and ketones such as acetone (SP value: 9.07, relative permittivity: 20.7), methyl ethyl ketone (SP value: 8.99), and cyclohexanone (SP value: 9.80).

The organic solvent dispersion of nanodiamonds according to the present invention, can hold the dispersibility of the nanodiamonds even when the concentration of the nanodiamond is adjusted high since the organic solvent dispersion contains the surface-modified nanodiamond exhibiting easy dispersibility in an organic solvent. The nanodiamond concentration (the total nanodiamond concentration including that of the surface-modified nanodiamond) in the organic solvent dispersion of nanodiamonds according to the present invention is, for example, 0.0001% by weight or more, preferably 0.001% by weight or more, and especially preferably 0.005% by weight or more. Here, the upper limit of the nanodiamond concentration is, for example, 5% by weight.

The organic solvent dispersion of nanodiamonds according to the present invention may contain nanodiamonds other than the surface-modified nanodiamond, but the proportion taken by the surface-modified nanodiamond in all the nanodiamonds contained in the organic solvent dispersion of nanodiamonds is, for example, 50% by weight or more, preferably 75% by weight or more, and especially preferably 95% by weight or more. Here, the upper limit is 100% by weight. Therefore, the content of nanodiamonds other than the surface-modified nanodiamond is, with respect to the total amount of nanodiamonds contained in the organic solvent dispersion of nanodiamonds, for example, 50% by weight or less, preferably 25% by weight or less, and especially preferably 5% by weight or less. When the content of the surface-modified nanodiamond is below the above range, it is likely to become difficult to obtain the organic solvent dispersion of nanodiamonds which contains nanodiamonds in a highly dispersed state.

The content (in the case of containing two or more kinds, their total amount) of the organic solvent in the total amount of the organic solvent dispersion of nanodiamonds according to the present invention is, for example, 85.0 to 99.5% by weight, and preferably 95.0 to 99.5% by weight.

The total content of the surface-modified nanodiamond and the organic solvent in the total amount of the organic solvent dispersion of nanodiamonds according to the present invention is, for example, 60% by weight or more, and preferably 90% by weight or more. Here, the upper limit is 100% by weight.

The organic solvent dispersion of nanodiamonds according to the present invention is excellent in dispersibility of the nanodiamonds in the organic solvent due to containing the above-described surface-modified nanodiamond.

Then, controlling the number of carbon atoms (specifically, the number of carbon atoms of R in the group represented by the formula (1)) of the surface modification group in the surface-modified nanodiamond according to the kind of the organic solvent is preferable in that the organic solvent dispersion of nanodiamonds having much better dispersibility can be obtained. For example, in the case of using the polar organic solvent (particularly a protonic polar organic solvent), it is preferable to use the surface-modified nanodiamond having the surface modification group in which R in the formula (1) is a straight-chain or branched-chain alkyl group having 1 to 9 (preferably 1 to 5) carbon atoms or a cycloalkyl group having 3 to 9 (preferably 3 to 5) carbon atoms. In the case of using the nonpolar organic solvent (particularly an aprotic nonpolar organic solvent), it is preferable to use the surface-modified nanodiamond having the surface modification group in which R in the formula (1) is a straight-chain or branched-chain alkyl group having 9 to (preferably 9 to 18) carbon atoms or a cycloalkyl group having 9 to 22 (preferably 9 to 18) carbon atoms.

The particle diameter D50 (median diameter) of the nanodiamonds in the organic solvent dispersion of nanodiamonds according to the present invention in the case of using the polar organic solvent as the organic solvent is, for example, 1000 nm or less, preferably 800 nm or less, and especially preferably 700 nm or less. The lower limit of the particle diameter D50 of the nanodiamonds is, for example, 100 nm.

The organic solvent dispersion of nanodiamonds according to the present invention can contain nanodiamonds in a highly dispersed state even in the case of using a solvent ordinarily having poor dispersion property as the organic solvent, namely, using, a protonic polar organic solvent or a nonpolar organic solvent, for using the surface-modified nanodiamonds.

The particle diameter D50 (median diameter) of the nanodiamonds in the organic solvent dispersion of nanodiamonds according to the present invention in the case of using the nonpolar organic solvent as the organic solvent is, for example, 1000 nm or less, preferably 100 nm or less, and especially preferably 30 nm or less. The lower limit of the particle diameter D50 of the surface-modified nanodiamonds is, for example, 4 nm.

The organic solvent dispersion of nanodiamonds according to the present invention is excellent in compatibility with oil agents and resin compositions; and by adding the organic solvent dispersion of nanodiamonds according to the present invention to the oil agents or the resin compositions, the nanodiamonds can be homogeneously dispersed in the oil agents or the resin compositions, and the characteristics originated from the nanodiamonds (for example, a high mechanical strength, electric insulation, and an excellent thermoconductivity, deodorant effect, antibacterial effect, and chemical resistance) can be imparted. In addition, the oil agents and the resin compositions containing the organic solvent dispersion of nanodiamonds added therein can suitably be used as heat radiating materials, optical materials (for example, high-functional film materials), material-reinforcing materials, heat exchange fluid media, coating materials (for example, antibacterial coating materials, and deodorant coating materials), abrasive materials, lubricants, medical materials, and the like.

EXAMPLES

Hereinafter, the present invention will be described specifically by way of Examples, but the present invention is not limited to these Examples. Here, pH was measured by using a pH meter (trade name: "La Com tester PH110", manufactured by Nikko Hansen & Co., Ltd.).

Preparation Example 1 (Preparation of Nanodiamonds to be Subjected to a Surface Modification Step)

Nanodiamond powder was prepared through the following formation step, refinement step, pH adjustment step, deagglutinating treatment step, centrifugal separation step, surface modification step, and drying step.

In the formation step, first, a molded explosive installed with an electric detonator is placed in the interior of a pressure vessel for detonation, and the vessel was hermetically closed in the state that an atmospheric composition gas at normal pressure and the explosive in use coexisted in the vessel. The vessel was an iron-made and the volume of the vessel was 15 m$^3$. The explosive used was 0.50 kg of a mixture of TNT with RDX (TNT/RDX (weight ratio)=50/50). Then, the electric detonator was initiated to detonate the explosive in the vessel. Then, by leaving the vessel to stand at room temperature for 24 hours, the temperature of the vessel and its interior was lowered. After the natural cooling, a nanodiamond crude product (containing agglutinates of nanodiamond particles and soot produced by the detonation method) adhered on the inner wall of the vessel was scraped off with a spatula to thereby recover the nanodiamond crude product. The recovery amount of the nanodiamond crude product was 0.025 kg.

Then, an acid treatment of the refinement step was carried out on the nanodiamond crude product obtained by carrying out the above-mentioned formation step a plurality of times. Specifically, 6 L of 10 wt % of hydrochloric acid was added to 200 g of the nanodiamond crude product to thereby obtain a slurry, which was then subjected to a heat treatment under reflux in a normal pressure condition for 1 hour. The heating temperature in the acid treatment was 85 to 100° C. Then, after cooling, water washing of solid contents (containing nanodiamond agglutinates and soot) was carried out by decantation. The water washing of the solid contents by decantation was carried out repeatedly until the pH of a precipitate liquid reached 2 from a low pH side.

Then, an oxidation treatment of the refinement step was carried out. Specifically, 5 L of an aqueous solution of 60 wt % of sulfuric acid and 2 L of an aqueous solution of 60 wt % of chromic acid were added to the precipitate liquid after decantation to thereby make a slurry, which was then subjected to a heat treatment under reflux in a normal pressure condition for 5 hours. The heating temperature in the oxidation treatment was 120 to 140° C. Then, after cooling, water washing of solid contents (containing nanodiamond agglutinates) was carried out by decantation. An initial supernatant liquid by the water washing was colored, but the water washing of the solid contents by decantation was repeatedly carried out until the supernatant liquid visually became transparent. Then, a precipitate liquid obtained by the final decantation in the repeated process was mixed with 1 L of an aqueous solution of 10 wt % of sodium hydroxide, and thereafter subjected to a heat treatment under reflux in a normal pressure condition for 1 hour. The heating temperature in this treatment was 70 to 150° C. Then, after cooling, a precipitate liquid was obtained by decantation, and 20 wt % hydrochloric acid was added to the precipitate liquid to adjust the pH to 2.5. Thereafter, water washing was carried out on solid contents in the precipitate liquid by a centrifugal sedimentation method.

Then, the pH adjustment step was carried out. Specifically, ultrapure water was added to a precipitate obtained through the water washing by a centrifugal sedimentation method to prepare a suspension of 8 wt % in solid content concentration, and thereafter, the pH of the suspension was adjusted to 10 by addition of sodium hydroxide. A slurry whose pH had been adjusted was thus obtained.

Then, the deagglutinating treatment step was carried out. Specifically, 300 mL of the slurry obtained in the preceding step was subjected to a deagglutinating treatment by using a bead mill (trade name: "Ultra Apecs Mill UAM-015", manufactured by Kotobuki Industry Co., Ltd.). In this treatment, deagglutinating media used were zirconia beads (diameter: 0.03 mm); the volume of the beads packed in a mill vessel was made to be 60% to the volume of the mill vessel; and the peripheral speed of a rotor pin rotating in the mill vessel was made to be 10 m/s. The deagglutinating treatment was carried out for 90 mins. with the flow rate of the slurry circulated in the apparatus of 10 L/h.

Then, the centrifugal separation step was carried out. Specifically, from a solution containing the nanodiamond having been subjected to the above-mentioned deagglutinating treatment step, coarse particles were removed by a classification operation utilizing the action of a centrifugal force (centrifugal separation treatment). In the centrifugal separation treatment of this step, the centrifugal force was set to be 20000×g, and centrifugation time was set to be 10 mins. Thereby, a black transparent nanodiamond water dispersion was obtained. The particle diameter of the nanodiamond particles contained in the water dispersion was measured by a dynamic light scattering method, and as a result, the median diameter (particle diameter D50) was 5.4 nm.

Then, powdering of the obtained nanodiamond water dispersion was carried out. Specifically, 100 mL of the nanodiamond water dispersion was spray dried. An apparatus used therefor was a spray drier (trade name: "B-290 type", manufactured by Nihon Buchi K. K.). Thereby, nanodiamond powder (ND) was obtained. The vacuum/heated IR thereof was measured. The result is shown in FIG. 1. Further, the powder (ND) was subjected to a thermogravimetry measurement by the following method. The result is shown in FIG. 5.

Example 1

Production of a surface-modified nanodiamond

A mixture of the nanodiamond powder (ND) (100 mg) obtained in Preparation Example 1 and acetonitrile (1.6 mL, 1.25 g) was subjected to an ultrasonic treatment. Then, an acetonitrile solution (1.5 mL) of a concentrated sulfuric acid (sulfuric acid concentration: 98% by weight) (92 mg) was added to the mixture. The resultant was stirred in a nitrogen atmosphere at 70° C. for 9 hours to thereby obtain a reaction mixture.

Acetonitrile (25 mL) was added to and mixed with the obtained reaction mixture, and the resulting mixture was subjected to an ultrasonic treatment and thereafter subjected to a centrifugal separation (20000×g, 10 minutes) to remove a supernatant liquid and recover a solid. Then, water (25 mL) was added to and mixed with the solid, and the resulting mixture was subjected to an ultrasonic treatment and thereafter subjected to a centrifugal separation (20000×g, 10 minutes) to remove a supernatant liquid (water washing) and recover a solid. The solid was recovered by repeating the water washing until the pH of the supernatant liquid became 6. Acetone (25 mL) was added to and mixed with the solid, and the resulting mixture was subjected to an ultrasonic treatment and thereafter subjected to a centrifugal separation (20000×g, 10 min). A supernatant liquid of this mixture was removed and a solid was recovered.

The recovered solid was subjected to a reduced-pressure heat drying (heating at 50° C. for 1 hour, thereafter, at 120° C. for 1 hour, in an environment of 1.5 kPa) and a gray solid (83.3 mg) was recovered. The gray solid was subjected to a vacuum/heated IR measurement and a peak of a methyl group was observed at 3104.83 cm$^{-1}$ (FIG. 2). Further, the gray solid was subjected to a thermogravimetry measurement by after-mentioned method. The result is shown in FIG. 5. From this, it was confirmed that the recovered gray solid was a surface-modified nanodiamond (ND—C$_1$) having a structure in which —NHCOCH$_3$ groups were bound to nanodiamond surfaces.

Organic solvent dispersion of nanodiamonds

Then, ethanol (SP value at 25° C. acquired by the Fedors method: 12.58, relative permittivity at 25° C.: 24.30) was added to and mixed with the recovered gray solid, and the resulting mixture was subjected to an ultrasonic treatment to thereby obtain an ethanol dispersion of nanodiamonds (nanodiamond concentration: 0.005% by weight). The particle diameter of the nanodiamonds in the ethanol dispersion of nanodiamonds was measured by a laser diffraction scattering method, and the median diameter (particle diameter D50) was 617 nm.

Example 2

Production of a surface-modified nanodiamond

A mixture of the nanodiamond powder (ND) (50.0 mg) obtained in Preparation Example 1 and decanenitrile (1.0 mL, 0.81 g) was subjected to an ultrasonic treatment. Then, the concentrated sulfuric acid (260 mg) was added to the mixture. The resultant was stirred in a nitrogen atmosphere at 130° C. for 8 hours to thereby obtain a reaction mixture.

Organic solvent dispersion of nanodiamonds

Toluene (SP value at 25° C. acquired by the Fedors method: 9.14, 25 mL, relative permittivity at 25° C.: 2.379) was added to and mixed with the obtained reaction mixture, and the resulting mixture was subjected to a centrifugal separation (20000×g, 10 mins) to remove a precipitate and thereby obtain a toluene dispersion of nanodiamonds (nanodiamond concentration: 0.3% by weight). The particle diameter of the nanodiamonds in the toluene dispersion of nanodiamonds was measured by a dynamic light scattering method, and the median diameter (particle diameter D50) was 27.8 nm.

Then, isopropyl alcohol (5 mL) was added to and mixed with the toluene dispersion liquid to cause the nanodiamonds to be precipitated. The resulting mixture was subjected to a centrifugal separation (20000×g, 10 mins) to remove a supernatant liquid, and a precipitate was recovered and dried to thereby obtain a gray solid. The gray solid was subjected to a vacuum/heated IR measurement, and peaks of a nonyl group were observed at 2913.91 cm$^{-1}$ and 2850.27 cm$^{-1}$, and a peak of an amido group was observed at 1670.05 cm$^{-1}$ (FIG. 3). Further, the gray solid was subjected to a thermogravimetry by after-mentioned method. The result is shown in FIG. 5. From this, it was confirmed that the recovered gray solid was a surface-modified nanodiamond (ND-C$_9$) having a structure in which —NHCO(CH$_2$)$_8$CH$_3$ groups were bound to nanodiamond surfaces.

Example 3

Production of a surface-modified nanodiamond

A mixture of the nanodiamond powder (ND) (100 mg) obtained in Preparation Example 1 and myristonitrile (1.25 g) was subjected to an ultrasonic treatment. Then, the concentrated sulfuric acid (120 mg) was added to the mixture. The resultant was stirred in a nitrogen atmosphere at 100° C. for 10 hours to thereby obtain a reaction mixture (containing a surface-modified nanodiamond (ND—C$_{13}$) having a structure in which —NHCO(CH$_2$)$_{12}$CH$_3$ groups were bound to nanodiamond surfaces).

Organic solvent dispersion of nanodiamonds

Toluene (25 mL) was added to and mixed with the obtained reaction mixture, and the resulting mixture was subjected to a centrifugal separation (20000×g, 10 mins) to remove a precipitate and thereby obtain a toluene dispersion of nanodiamonds (nanodiamond concentration: 0.3% by weight). The particle diameter of the nanodiamonds in the toluene dispersion of nanodiamonds was measured by a dynamic light scattering method, and the median diameter (particle diameter D50) was 25.6 nm.

Then, isopropyl alcohol (5 mL) was added to and mixed with the toluene dispersion liquid to cause the nanodiamonds to be precipitated. The resulting mixture was subjected to a centrifugal separation (20000×g, 10 mins) to remove a supernatant liquid, and a precipitate was recovered and dried to thereby obtain a gray solid. The gray solid was subjected to a thermogravimetry by after-mentioned method. The result is shown in FIG. 5.

Example 4

Production of a surface-modified nanodiamond

A mixture of the nanodiamond powder (ND) (130 mg) obtained in Preparation Example 1 and nonadecanenitrile (4.67 g) was heated to 50° C. to cause the nonadecanenitrile to melt. Then, the concentrated sulfuric acid (210 mg) was added to the mixture. The resultant was stirred in a nitrogen atmosphere at 130° C. for 8 hours to thereby obtain a reaction mixture.

Acetone (25 mL) was added to and mixed with the obtained reaction mixture. The resulting mixture was subjected to an ultrasonic treatment, and thereafter subjected to a centrifugal separation (20000×g, 10 mins) to remove a supernatant liquid and recover a solid. Then, ethanol (25 mL) was added to the solid. The resulting mixture was subjected to an ultrasonic treatment, and thereafter subjected to a centrifugal separation (20000×g, 10 mins) to remove a supernatant liquid and a solid was recovered.

Organic solvent dispersion of nanodiamonds

Toluene (25 mL) was added to and mixed with the obtained solid, and the resulting mixture was subjected to a centrifugal separation (20000×g, 10 mins) to remove a precipitate and thereby obtain a toluene dispersion of nanodiamonds (nanodiamond concentration: 0.35% by weight). The particle diameter of the nanodiamonds in the toluene dispersion of nanodiamonds was measured by a dynamic light scattering method, and the median diameter (particle diameter D50) was 26.7 nm.

Then, isopropyl alcohol (5 mL) was added to and mixed with the toluene dispersion liquid to cause the nanodiamonds to be precipitated. The resulting mixture was subjected to a centrifugal separation (20000×g, 10 mins) to remove a supernatant liquid, and a precipitate was recovered and dried to thereby obtain a gray solid. The gray solid was subjected to a vacuum/heated IR measurement, and peaks of an octadecyl group were observed at 2923.56 cm$^{-1}$ and 2854.13 cm$^{-1}$ and peaks of an amido group were observed at 1700.01 cm$^{-1}$ and 1688.55 cm$^{-1}$ (FIG. 4). Further, the gray solid was subjected to a thermogravimetry by aftermentioned method. The result is shown in FIG. 5. From this, it was confirmed that the recovered gray solid was a surface-modified nanodiamond (ND—$C_{18}$) having a structure in which —NHCO($CH_2$)$_{17}CH_3$ groups were bound to nanodiamond surfaces.

Example 5
Production of a surface-modified nanodiamond

A mixture of the nanodiamond powder (ND) (100 mg) obtained in Preparation Example 1 and nonadecanenitrile (2.01 g) was heated to 50° C. to cause the nonadecanenitrile to melt. Then, the concentrated sulfuric acid (230 mg) was added to the mixture. The resultant was stirred in a nitrogen atmosphere at 220° C. for 8 hours to thereby obtain a reaction mixture.

Toluene (SP value at 25° C. obtained by the Fedors method: 9.14, 25 mL, relative permittivity at 25° C.: 2.379) was added to and mixed with the reaction mixture, and the resulting mixture was subjected to a centrifugal separation (20000×g, 10 mins) to remove a precipitate and thereby obtain a toluene dispersion of nanodiamonds (nanodiamond concentration: 0.4% by weight). The particle diameter of the nanodiamonds in the toluene dispersion of nanodiamonds was measured by a dynamic light scattering method, and the median diameter (particle diameter D50) was 10.4 nm.

Method of measuring the median diameter by the laser diffraction scattering method The median diameter was measured, as a 50%-volume-cumulative diameter at refractive indices of 2.40 to 0.20, by a laser diffraction type particle size distribution analyzer (model name: "SALD-2000"), manufactured by Shimadzu Corp.). The nanodiamond concentration of the organic solvent dispersion of nanodiamonds subjected to the measurement was 0.005% by weight.

Method of measuring the median diameter by the dynamic light scattering method

The median diameter was measured, as a 50%-volume-cumulative diameter, by an apparatus (trade name: "Zetasizer Nano ZS"), manufactured by Spectris Co., Ltd. The nanodiamond concentration of the organic solvent dispersion of nanodiamonds subjected to the measurement was 0.3% by weight.

Method of the Thermogravimetry

The weight loss of a sample was measured by heating the sample (about 3 mg) in an air atmosphere at a temperature-rise rate of 20° C./min using a TG/DTA (thermogravimetry/differential thermal analysis) apparatus (trade name: EXSTAR6300", manufactured by SII Nano Technology Inc.). Here, a reference material used was alumina.

INDUSTRIAL APPLICABILITY

The surface-modified nanodiamond according to the present invention exhibits easy dispersibility in an organic solvent. Hence, by subjecting a mixture of the surface-modified nanodiamond according to the present invention and the organic solvent to a dispersion treatment, an organic solvent dispersion of nanodiamonds which contains nanodiamonds in a highly dispersed state can be obtained.

Then, the organic solvent dispersion of nanodiamonds is excellent in compatibility with oil agents and resin compositions; and compositions obtained by adding the organic solvent dispersion of nanodiamonds to the oil agents and the resin compositions are suitably used as heat radiating materials, optical materials, material-reinforcing materials, heat exchange fluid media, coating materials, abrasive materials, lubricants, medical materials, and the like.

The invention claimed is:

1. A surface-modified nanodiamond comprising:
   a nanodiamond; and
   a group being bound to a particulate surface of the nanodiamond and represented by formula (1):

—NHCOR (1)

wherein R is an organic group having a carbon atom at a binding site with a neighboring carbonyl carbon atom indicated in the formula; and the left end, in the formula, of the group serves to form bonding to the nanodiamond.

2. The surface-modified nanodiamond according to claim 1, wherein the nanodiamond is a detonation nanodiamond or a high-temperature high-pressure nanodiamond.

3. The surface-modified nanodiamond according to claim 1 or 2, wherein R in the formula (1) represents a straight-chain or branched-chain alkyl group having 1 to 22 carbon atoms or a 3- to 22-membered cycloalkyl group.

4. An organic solvent dispersion of nanodiamonds, being made by dispersing the surface-modified nanodiamond according to claim 1 in an organic solvent.

5. The organic solvent dispersion of nanodiamonds according to claim 4, wherein the organic solvent has an SP value [(cal/cm$^3$)$^{0.5}$: Fedors calculation value] at 25° C. of 7 to 23.

6. The organic solvent dispersion of nanodiamonds according to claim 4 or 5, wherein the organic solvent has a relative permittivity at 25° C. of 1 to 40.

7. A method for producing a surface-modified nanodiamond, the method comprising:
   reacting a nanodiamond with a nitrile compound in the presence of an acid catalyst to obtain the surface-modified nanodiamond according to claim 1, the nitrile compound being represented by formula (2):

R—CN (2)

wherein R is an organic group having a carbon atom at a binding site with a cyano group indicated in the formula.

8. The method for producing a surface-modified nanodiamond according to claim 7, wherein the reaction of the nanodiamond with the nitrile compound represented by the formula (2) is carried out after a deagglutinating and/or crushing treatment for the nanodiamond or during a deagglutinating and/or crushing treatment for the nanodiamond.

* * * * *